(12) United States Patent
Grass

(10) Patent No.: US 7,964,658 B2
(45) Date of Patent: Jun. 21, 2011

(54) DIALKYL TEREPHTHALATES AND THEIR USE

(75) Inventor: Michael Grass, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 232 days.

(21) Appl. No.: 11/622,567

(22) Filed: Jan. 12, 2007

(65) Prior Publication Data
US 2007/0179229 A1   Aug. 2, 2007

(30) Foreign Application Priority Data
Jan. 12, 2006   (DE) .................. 10 2006 001 795

(51) Int. Cl.
C08K 5/12 (2006.01)
C08K 5/10 (2006.01)
C08L 27/06 (2006.01)
C07C 69/82 (2006.01)
C07C 69/76 (2006.01)

(52) U.S. Cl. ........ 524/296; 524/287; 524/321; 524/569; 560/8; 560/76; 560/103

(58) Field of Classification Search .................. 524/285, 524/287, 567, 569, 296, 321; 560/3, 130, 560/127, 8, 103, 76
See application file for complete search history.

(56) References Cited

U.S. PATENT DOCUMENTS

| 3,224,995 | A | 12/1965 | De Pree |
| 7,323,586 | B2 | 1/2008 | Wiese et al. |
| 7,323,588 | B2 | 1/2008 | Grass et al. |
| 7,638,568 | B2 | 12/2009 | Grass et al. |
| 2003/0114718 | A1* | 6/2003 | Knoop et al. ................. 568/855 |
| 2004/0238787 | A1 | 12/2004 | Wiese et al. |
| 2004/0260113 | A1 | 12/2004 | Bueschken et al. |
| 2005/0038285 | A1 | 2/2005 | Maschmeyer et al. |
| 2005/0049341 | A1 | 3/2005 | Grass et al. |
| 2005/0101800 | A1 | 5/2005 | B schken et al. |
| 2006/0167151 | A1 | 7/2006 | Grass et al. |
| 2007/0010599 | A1* | 1/2007 | Grass et al. ................... 523/160 |
| 2007/0037926 | A1* | 2/2007 | Olsen et al. ................... 524/569 |
| 2007/0060768 | A1 | 3/2007 | Grass et al. |
| 2007/0287781 | A1* | 12/2007 | Grass et al. ................... 524/308 |
| 2008/0188601 | A1* | 8/2008 | Grass et al. ................... 524/321 |

FOREIGN PATENT DOCUMENTS

| DE | 199 27 978 A1 | 12/2000 |
| JP | 2001-31794 | 2/2001 |
| JP | 2003-301082 | 10/2003 |
| WO | WO 2007/021987 A1 | 2/2007 |

OTHER PUBLICATIONS

Jay Nematollahi, et al. "Plasticizers in Medical Application I. Analysis and Toxicity Evaluation of DIALKYL1 Benzenedicarboxylates", Journal of Pharmaceutical Sciences, XP-009080785, vol. 56, No. 11, Nov. 1967, pp. 1446-1453.
A. Don Beeler, Terephthalate Esters: A New Class of Plasticizers for Polyvinyl Chloride, SPE Annual Technical Conference and Exhibition, XP-008040735, Apr. 26, 1976, pp. 613-615.

* cited by examiner

Primary Examiner — Mark Eashoo
Assistant Examiner — Michael Pepitone
(74) Attorney, Agent, or Firm — Oblon, Spivak, McClelland, Maier & Neustadt, L.L.P.

(57) ABSTRACT

A plasticizer capable of fast gelling and capable of imparting storage stability on plastisols contains dialkyl terephthalate, wherein the alkyl radicals of said dialkyl terephthalate have a longest carbon chain of at least 4 carbon atoms and have a total number of carbon atoms per alkyl radical of 5.

13 Claims, 1 Drawing Sheet

DIALKYL TEREPHTHALATES AND THEIR USE

BACKGROUND OF THE INVENTION

1. Field of the Invention

The present invention relates to dialkyl terephthalates wherein the alkyl stands for alkyl radicals which have a longest carbon chain of at least 4 carbon atoms, to a process for preparing them, and to the use of these products.

2. Description of the Related Art

Polyvinyl chloride (PVC) is one of the most important polymers industrially. It is used in a wide variety of applications, in the form of either unplasticized (rigid) PVC or plasticized (flexible) PVC.

To produce a plasticized PVC, plasticizers are added to the PVC, and in the majority of cases use is made of phthalates, in particular di-2-ethylhexyl phthalate (DEHP), diisononyl phthalate (DINP), and diisodecyl phthalate (DIDP). As the chain length of the esters increases, the solution or gelling temperatures rise, and the processing temperatures of the plasticized PVC therefore rise. The process temperatures can be reduced again by adding what are known as fast-gellers, such as the short-chain phthalates dibutyl phthalate (DBP), diisobutyl phthalate (DIBP), benzylbutyl phthalate (BBP) or diisoheptyl phthalate (DIHP).

Owing to debates concerning reproductive toxicities, which in a number of cases have already led to increased labeling under laws which regulate hazardous substances, it must be assumed that, in the future, the use of these shorter-chain phthalates will go down significantly. There is therefore a need for plasticizers which are not subject to mandatory labeling but which can be used as fast-gellers and which are produced from raw materials available worldwide in large quantities.

Besides phthalic acid, terephthalic acid, or its dimethyl terephthalate derivative, represents a compound which, with an estimated annual production of the order of millions of tons, is available in large quantities. An example of a product mass-produced starting from terephthalic acid is polyethylene terephthalate (PET). To date, however, only one monomeric ester of terephthalic acid has acquired some significance industrially as a plasticizer for PVC, namely di-2-ethylhexyl terephthalate (DEHT or else DOTP), which is marketed by Eastman Chemical for example.

U.S. Pat. No. 5,071,690 describes the possibility of using di-n-butyl terephthalate as a plasticizer for producing polyester films. U.S. Pat. No. 6,051,305 describes the use of thermoplastic polymer particles containing dibutyl terephthalate, as toner particles.

Don Beeler in Soc. Plast. Eng., Tech. Pap. 22 (1976), 613 15 describes how terephthalic esters of alcohols having from 1 to 6 carbon atoms are with just one exception (diisopropyl terephthalate) all solids and are incompatible with PVC. Consequently, in spite of the statement that the pattern of properties of terephthalic esters corresponds essentially to that of phthalic esters longer by one carbon atom in the alcohol chain, it could not have been anticipated that terephthalic esters of alcohols having a chain length of from 4 to 6 carbon atoms might be fast-geller candidates.

SUMMARY OF THE INVENTION

It is an object of the present invention, to provide a plasticizer which can be used as a fast-geller and which preferably, when used in plastisols, also endows them with a certain stability on storage, i.e., which has the effect of only a slight increase in viscosity over time.

This and other objects have been achieved by the present invention the first embodiment of which includes a plasticizer, comprising:
  dialkyl terephthalate,
  wherein the alkyl radicals of said dialkyl terephthalate have a longest carbon chain of at least 4 carbon atoms and have a total number of carbon atoms per alkyl radical of 5.

In another embodiment, the present invention relates to a composition, comprising:
  a dialkyl terephthalate, and
  a polymer selected from the group consisting of PVC, PVB, PAMA, homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, styrene, acrylonitrile, cyclic olefins and mixtures thereof,
  wherein the alkyl radicals of the dialkyl terephthalate have a longest carbon chain of at least 4 carbon atoms and have a total number of carbon atoms per alkyl radical of from 4 to 5.

In yet another embodiment, the present invention provides a process for preparing a dialkyl terephthalate, comprising
  a) hydroformylating $C_3$ or $C_4$ olefins to give $C_4$ or $C_5$ aldehydes, respectively,
  b) hydrogenating the aldehydes obtained in step a) to the corresponding alcohols, and
  c) reacting the alcohols from b) with terephthalic acid or with a derivative of terephthalic acid to the corresponding diester,
  wherein said dialkyl terephthalate has alkyl radicals which have a longest carbon chain of at least 4 carbon atoms and have a total number of carbon atoms per alkyl radical of from 4 to 5.

In another embodiment, the present invention provides a plasticizer, comprising:
  a dialkyl terephthalate, and
  a polymer selected from the group consisting of PVC, PVB, PAMA, homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, styrene, acrylonitrile, cyclic olefins and mixtures thereof,
  wherein the alkyl radicals of the dialkyl terephthalate have a longest carbon chain of at least 4 carbon atoms and have a total number of carbon atoms per alkyl radical of from 4 to 5.

In yet another embodiment, the present invention provides an adhesive, comprising:
  a dialkyl terephthalate, and
  wherein the alkyl radicals of the dialkyl terephthalate have a longest carbon chain of at least 4 carbon atoms and have a total number of carbon atoms per alkyl radical of from 4 to 5.

In another embodiment, the present invention provides a sealing composition, comprising:
  a dialkyl terephthalate, and
  wherein the alkyl radicals of the dialkyl terephthalate have a longest carbon chain of at least 4 carbon atoms and have a total number of carbon atoms per alkyl radical of from 4 to 5.

In another embodiment, the present invention provides a paint, comprising:

a dialkyl terephthalate, and wherein the alkyl radicals of the dialkyl terephthalate have a longest carbon chain of at least 4 carbon atoms and have a total number of carbon atoms per alkyl radical of from 4 to 5.

In another embodiment, the present invention provides an ink, comprising:

a dialkyl terephthalate, and wherein the alkyl radicals of the dialkyl terephthalate have a longest carbon chain of at least 4 carbon atoms and have a total number of carbon atoms per alkyl radical of from 4 to 5.

DETAILED DESCRIPTION OF THE INVENTION

Figure 1:
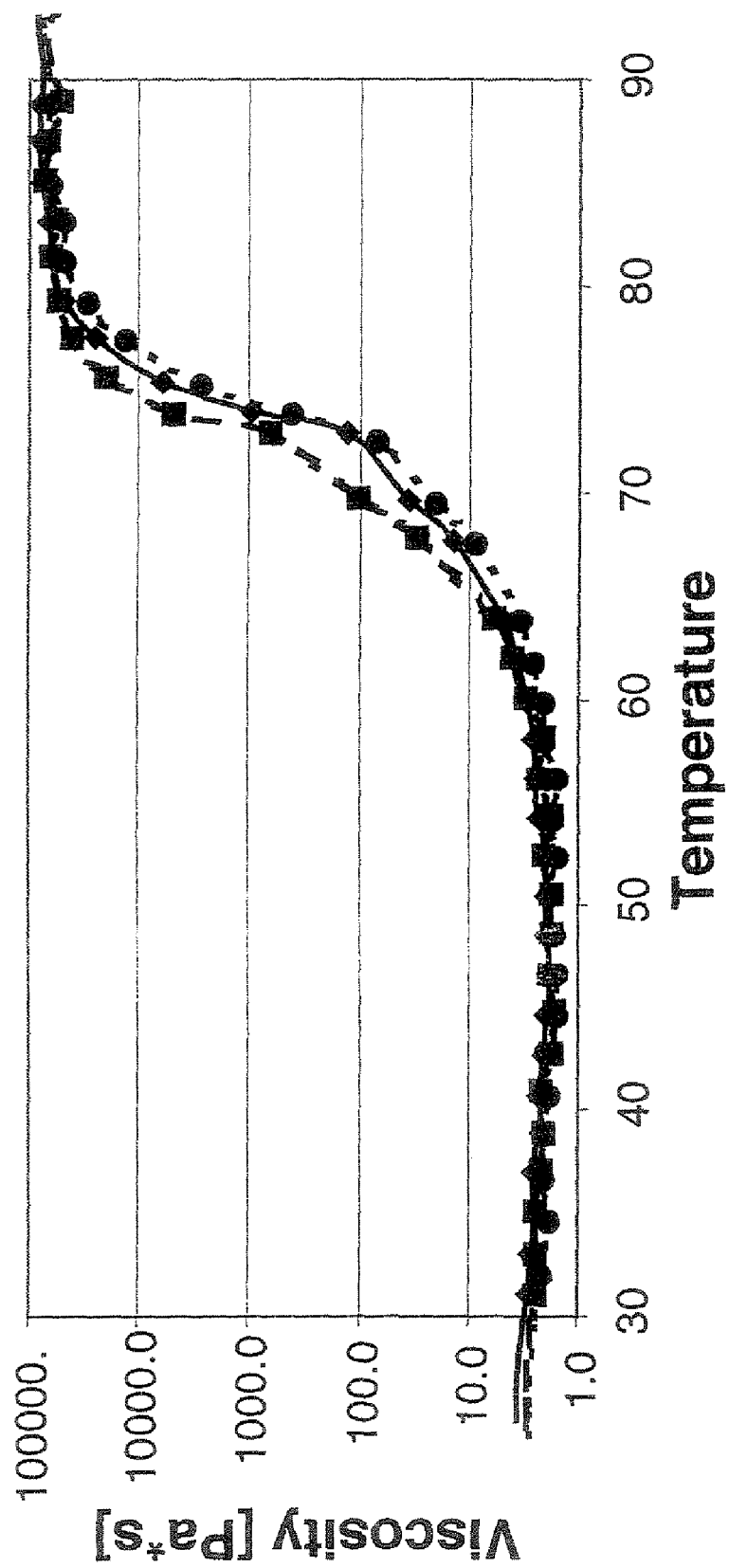
FIG. 1 shows the section of the viscosity/temperature curve ("gelling curve") which is relevant for the onset of gelling in the measurements carried out in Example 5.

Surprisingly it has been found that terephthalic esters having from 4 to 5 carbon atoms in the longest carbon chain of the alcohol are highly suitable for use as (fast-gelling) plasticizers. This is particularly surprising in view of Don Beeler's view that such terephthalic esters would be incompatible with PVC.

The present invention accordingly provides plasticizers, and plasticizer compositions, containing dialkyl terephthalate, wherein the alkyl radicals have a longest carbon chain of at least 4 carbon atoms and a total number of carbon atoms per alkyl radical of 5.

Likewise provided by the present invention is the use of dialkyl terephthalates as plasticizers in compositions containing a polymer selected from PVC, PVB, PAMA or homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, styrene, acrylonitrile or cyclic olefins, wherein the alkyl radicals of the dialkyl terephthalate have a longest carbon chain of at least 4 carbon atoms and have a total number of carbon atoms per alkyl radical of from 4 to 5, in particular 4 or 5.

Additionally provided by the present invention is a composition containing a plasticizer and a polymer selected from PVC, PVB, PAMA or homopolymers or copolymers based on ethylene, propylene, butadiene, vinyl acetate, glycidyl acrylate, glycidyl methacrylate, methacrylates, acrylates, acrylates in which attached to the oxygen atom of the ester group there are alkyl radicals of branched or unbranched alcohols having from one to ten carbon atoms, styrene, acrylonitrile, cyclic olefins, wherein the composition comprises as plasticizer dialkyl terephthalate in which the alkyl radicals have a longest carbon chain of at least 4 carbon atoms and a total number of carbon atoms per alkyl radical of from 4 to 5, in particular 4 or 5, and also a process for preparing dialkyl terephthalates whose alkyl radicals have a longest carbon chain of at least 4 carbon atoms and a total number of carbon atoms per alkyl radical of from 4 to 5, in particular 4 or 5, comprising the steps of a) hydroformylating $C_3$ or $C_4$ olefins to give $C_4$ or $C_5$ aldehydes, respectively, b) hydrogenating the aldehydes obtained in step a) to the corresponding alcohols, and c) reacting the alcohols from b) with terephthalic acid or with a derivative of terephthalic acid to the corresponding diester.

The plasticizers of the present invention have the advantage that when used in plastisols, they have a good stability on storage. Use of the plasticizers of the present invention is especially advantageous on account of the effective gelling they produce. Depending on the end use it is possible to employ plasticizers of the present invention containing a dialkyl terephthalate in which the alkyl radicals have a longest carbon chain of at least 4 carbon atoms and a total number of carbon atoms per alkyl radical of 4 or 5, in which case, depending on the total number of carbon atoms in the alkyl radical, the gelling properties are improved or the volatility is reduced. The plasticizers of the present invention are particularly suitable for use in plastisols, since they allow the plastisol to have a low viscosity. A further advantage is that the plasticizer of the present invention can be used as a substitute for diisobutyl phthalate, di-n-butyl phthalate, dipentyl phthalate or diisoheptyl phthalate, since it allows comparable mechanical properties to be obtained. The plasticizer of the invention, and compositions containing dialkyl terephthalates in which the alkyl radicals have a longest carbon chain of at least 4 carbon atoms and a total number of carbon atoms per alkyl radical of 4 or 5, have the further advantage that they are based on terephthalic acid and not on phthalic acid. Diesters of phthalic acid, particularly 2 ethylhexyl phthalates, are said by James L. Cooper (in the paper "An Alternative to DEHP in Plasticized PVC", at the Vinyl Formulators Division, 16th Annual Compounding Conference, Harrah's/Harvey's Resort, Lake Tahoe, Nev., Jul. 17 to 19, 2005) to differ in metabolism from the diesters of terephthalic acid. On degradation, the terephthalates are first hydrolyzed completely to alcohol and terephthalic acid, whereas the phthalates are hydrolyzed only to the monoester. These monoesters have been identified in laboratory studies as one of the toxicologically active substances. Owing to the difference in metabolism between di-2-ethylhexyl phthalate and di-2-ethylhexyl terephthalate, the latter is said by James L. Cooper to have a significantly lower toxicity than di-2-ethylhexylphthalate. Because the plasticizers of the present invention are based on terephthalic acid it can be assumed that, on degradation of the terephthalates present in accordance with the invention, there will be complete hydrolysis to terephthalic acid and hence the terephthalates will likewise have a lower toxicity than the corresponding phthalates.

In the text below, the present invention is described on an exemplary basis, without any intention that this exemplary description should restrict the invention, whose scope of protection is given by the claims and the description. The claims themselves are also part of the disclosure content of the present invention. Where ranges, general formulae or classes of compound are specified below, the disclosure is intended to encompass not only the corresponding ranges or groups of compounds that are mentioned explicitly, but additionally all subranges and subgroups of compounds which, while they may be obtained by omitting individual values (ranges) or compounds, have not been explicitly mentioned, for reasons of greater ease of comprehension.

A feature of the plasticizer of the present invention and of the plasticizer composition of the present invention (referred to below, for the sake of simplicity, simply as plasticizer), containing dialkyl terephthalate, is that the alkyl radicals have a longest carbon chain of at least 4 carbon atoms and have a total number of carbon atoms per alkyl radical of 5. In one ester molecule the alkyl radicals can be the same or different. Where isomerically pure alcohols are not used for the preparation of the esters, the products are usually dialkyl terephthalate mixtures containing ester molecules which have different alkyl radicals.

Preferably more than 60% (% by mass, based on the sum of the alkyl radicals) of the alkyl radicals in the dialkyl terephthalates are n-pentyl radicals. More preferably from 70% to 99.9% of the alkyl radicals in the dialkyl terephthalates are n pentyl radicals and from 30% to 0.1% are methylbutyl radicals, especially 2-methylbutyl radicals; with particular preference from 85% to 98% are n-pentyl radicals and from 15% to 2% are methylbutyl radicals, especially 2-methylbutyl radicals, and, with very particular preference, from 90% to 96% are n-pentyl radicals and from 10% to 4% are methylbutyl radicals, especially 2-methylbutyl radicals. Preferably more than 50%, more preferably more than 75%, and very preferably more than 95% of the methylbutyl radicals are 2-methylbutyl radicals. The percentage distribution of the C5 alkyl radicals is easy to ascertain, by hydrolyzing the esters and separating off the resulting alcohol and subjecting it to analysis by gas chromatography (GC). By way of example the gas-chromatographic separation can be carried out on a polydimethylsiloxane column (e.g. DB 5) as stationary phase with a length of 60 m, an internal diameter of 0.25 mm, and a film thickness of 0.25 μm.

It can be advantageous if the plasticizers of the present invention contain, in addition to dialkyl terephthalate having a total number of carbon atoms of 5 per alkyl radical, at least one primary plasticizer. Primary plasticizers are compounds which can be used as sole plasticizers and which across wide concentration ranges (a few percent, e.g., 10% by mass through to ratios with more plasticizer than polymer) are compatible with the polymer to be plasticized. The presence of primary plasticizers allows the properties of the plasticizer of the present invention to be varied. The plasticizer of the present invention preferably contains, in addition to dialkyl terephthalate having a total number of carbon atoms of 5 per alkyl radical, at least one primary plasticizer selected from dialkyl phthalates, trialkyl trimellitates, dialkyl adipates, dialkyl terephthalates, alkyl 1,2-cyclohexanedicarboxylates, alkyl 1,3 cyclohexanedicarboxylates, and alkyl 1,4-cyclohexanedicarboxylates where alkyl=alkyl radical having from 7 to 11, in particular from 8 to 10, carbon atoms, the glycol dibenzoates, and the alkylsulfonic esters of phenol where alkyl=alkyl radical having from 8 to 22 carbon atoms, and also acylated and nonacylated trialkyl citrates, polymeric plasticizers, and glycerol esters.

The fraction of primary plasticizers in the plasticizer of the present invention is preferably from 20% to 99% by mass, more preferably from 25% to 80% by mass, and very preferably from 30% to 75% by mass, based on the total mass of all the plasticizers employed. The fraction of primary plasticizers includes all values and subvalues therebetween, especially including 25, 30, 35, 40, 45, 50, 55, 60, 65, 70, 75, 80, 85, 90 and 95% by mass.

It can be advantageous if the plasticizer of the invention, in addition to dialkyl terephthalates having a total number of carbon atoms of 5 per alkyl radical, contains at least one alkyl benzoate where alkyl=alkyl radical having from 7 to 13, in particular from 8 to 10, carbon atoms, preferably nonyl or isononyl benzoate and more preferably isononyl benzoate. The fraction of alkyl benzoate where alkyl=alkyl radical having 8 to 10 carbon atoms, in particular of isononyl benzoate, in the plasticizer of the present invention is preferably from 5% to 90% by mass, more preferably from 10% to 80% by mass, and very preferably from 30% to 70% by mass. The fraction of alkyl benzoate includes all values and subvalues therebetween, especially including 10, 15, 20, 25, 30, 35, 40, 45, 50, 55, 60, 65, 70, 75, 80 and 85% by mass.

With particular preference the plasticizer of the invention, besides dialkyl terephthalates having a total number of carbon atoms of 5 per alkyl radical and at least one alkyl benzoate where alkyl=alkyl radical having from 8 to 10, preferably 9, carbon atoms, contains at least one primary plasticizer. Plasticizers of the present invention of this kind preferably have a fraction of dialkyl terephthalates having a total number of carbon atoms of 5 per alkyl radical of from 5% to 70% by mass, a fraction of alkyl benzoate where alkyl=alkyl radical having from 8 to 10 carbon atoms of from 5% to 70% by mass, and a fraction of primary plasticizers of from 20% to 90% by mass. The fraction of dialkyl terephthalates having a total number of carbon atoms of 5 per alkyl radical includes all values and subvalues therebetween, especially including 10, 15, 20, 25, 30, 35, 40, 45, 50, 55, 60 and 65% by mass. The fraction of alkyl benzoate where alkyl=alkyl radical having from 8 to 10 carbon atoms includes all values and subvalues therebetween, especially including 10, 15, 20, 25, 30, 35, 40, 45, 50, 55, 60 and 65% by mass. The fraction of primary plasticizers includes all values and subvalues therebetween, especially including 25, 30, 35, 40, 45, 50, 55, 60, 65, 70, 75, 80 and 85% by mass. A feature of the inventive use of dialkyl terephthalate as a plasticizer in compositions comprising a polymer selected from PVC, PVB, PAMA or homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, styrene, acrylonitrile, cyclic olefins, or in adhesives, paints or varnishes, is that the alkyl radicals of the dialkyl terephthalate used have a longest carbon chain of at least 4 carbon atoms and have a total number of carbon atoms per alkyl radical of from 4 to 5, in particular 4 or 5.

It can be advantageous if the total number of carbon atoms per alkyl radical of the dialkyl terephthalates used as plasticizers is 5. These plasticizers of the present invention have the advantage over the dialkyl terephthalates in which the alkyl radicals have a total number of carbon atoms per alkyl radical of 4 of a lower volatility.

Preference is given to using dialkyl terephthalates more than 60% (% by mass, based on the sum of the alkyl radicals) of whose alkyl radicals are n pentyl radicals. By dialkyl terephthalates here are also meant mixtures of dialkyl terephthalates containing dialkyl terephthalates having different alkyl radicals. More preference is given to using dialkyl terephthalates from 70% to 99.9% (% by mass, based on the sum of the alkyl radicals) of whose alkyl radicals are n pentyl radicals and from 30% to 0.1% are methylbutyl radicals, especially 2-methylbutyl radicals, particular preference to those from 85% to 98% of whose alkyl radicals are n-pentyl radicals and from 15% to 2% are methylbutyl radicals, especially 2-methylbutyl radicals, and very particular preference to those from 90% to 95% of whose alkyl radicals are n-pentyl radicals and from 10% to 5% are methylbutyl radicals, especially 2-methylbutyl radicals. Preferably more than 50%, more preferably more than 75%, and very preferably more than 95% of the methylbutyl radicals are 2-methylbutyl radicals. The aforementioned ranges are especially preferred when using, in accordance with the invention, dialkyl terephthalates which have a total number of carbon atoms per alkyl radical of 5. The percentage distribution of the C5 alkyl radicals can be readily ascertained by hydrolyzing the esters and by separating off the resulting alcohol and subjecting it to analysis by gas chromatography (GC).

It can also be advantageous if the dialkyl terephthalates used as plasticizers are those in which the total number of carbon atoms per alkyl radical is 4. These plasticizers of the present invention have the advantage over the dialkyl terephthalates in which the alkyl radicals have a total number of carbon atoms per alkyl radical of 5 of more effective gelling.

The plasticizers of the invention, or the dialkyl terephthalates which have a longest carbon chain of at least 4 carbon atoms and a total number of carbon atoms per alkyl radical of from 4 to 5, in particular 4 or 5, can be used, for example, as viscosity reducers and fast-gelling plasticizers. In comparison with known systems for modifying polymers such as PVC, they score by their good storage stability in plastisols. The plasticizers of the invention, or the dialkyl terephthalates which have a longest carbon chain of at least 4 carbon atoms and a total number of carbon atoms per alkyl radical of from 4 to 5, in particular 4 or 5, can be used, for example, in paints and varnishes, sealing compounds, in adhesives or components of adhesives, or in plastics or components of plastics. The plasticizers of the invention, or the aforementioned dialkyl terephthalates, are used with preference as plasticizers in plastics, such as PVC, polyalkyl methacrylates (PAMA) or PVB, for example. More preferably they are used, for example, in PVC plastisols or PAMA plastisols. With particular preference they are employed in blends with what are known as primary plasticizers. Primary plasticizers are those which can be used as sole plasticizers and which across wide concentration ranges are compatible with the polymer. Examples of these primary plasticizers include dialkyl phthalates, dialkyl terephthalates, and trialkyl trimellitates each possessing from 7 to 11 carbon atoms in the alkyl side chain. Additionally included among these primary plasticizers are the cyclohexanedicarboxylic esters or cyclohexanetricarboxylic esters, which are preparable from these stated products by means, for example, of ring hydrogenation. Further primary plasticizers that may be mentioned here include the following: alkylsulfonic esters of phenol (e.g., brand name MESAMOLL or MESAMOLL II), glycol dibenzoates, glycerol esters, acylated or nonacylated trialkyl citrates, polymeric plasticizers.

Through the use of the dialkyl terephthalates in which the alkyl radicals of the dialkyl terephthalate used have a longest carbon chain of at least 4 carbon atoms and have a total number of carbon atoms per alkyl radical of from 4 to 5, in particular 4 or 5, as plasticizers it is possible to obtain corresponding compositions. These compositions, containing a plasticizer and a polymer selected from PVC, PVB, PAMA or homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, or styrene, acrylonitrile or cyclic olefins, are in fact notable in that they contain as plasticizer a dialkyl terephthalate in which the alkyl radicals have a longest carbon chain of at least 4 carbon atoms and a total number of carbon atoms per alkyl radical of from 4 to 5, in particular 4 or 5.

It can be advantageous if the composition of the present invention contains, as plasticizers, dialkyl terephthalates in which the alkyl radicals of the dialkyl terephthalate have a total number of carbon atoms per alkyl radical of 4. Preferably a composition of this kind contains a dialkyl terephthalate from 70% to 100% (% by mass based on the sum of the alkyl radicals) of whose alkyl radicals are n-butyl radicals, preferably from 85% to 99.9% of which are n-butyl radicals. The dialkyl terephthalate includes all values and subvalues therebetween, especially including 75, 80, 85, 90 and 95% by mass. These plasticizers of the present invention have the advantage of producing better gelling than the dialkyl terephthalates in which the alkyl radicals have a total number of carbon atoms per alkyl radical of 5.

It can be particularly advantageous if the composition of the present invention contains, as plasticizers, dialkyl terephthalates in which the alkyl radicals of the dialkyl terephthalate have a total number of carbon atoms per alkyl radical of 5. These plasticizers of the present invention have the advantage of having lower volatility than the dialkyl terephthalates in which the alkyl radicals have a total number of carbon atoms per alkyl radical of 4.

The composition of the present invention preferably comprises dialkyl terephthalates more than 60% (% by mass based on the sum of the alkyl radicals) of whose alkyl radicals are n-pentyl radicals. Dialkyl terephthalates are taken here to include mixtures of dialkyl terephthalates containing dialkyl terephthalates with different alkyl radicals. More preferably the compositions of the present invention comprise dialkyl terephthalates from 70% to 99.9% of whose alkyl radicals are n pentyl radicals and from 30% to 0.1% are methylbutyl radicals, especially 2-methylbutyl radicals, very preferably from 85% to 98% are n-pentyl radicals and from 15% to 2% are methylbutyl radicals, especially 2-methylbutyl radicals, and with particular preference from 90% to 96% are n pentyl radicals and from 10% to 4% are methylbutyl radicals, especially 2-methylbutyl radicals. Of the methylbutyl radicals, preferably more than 50%, more preferably more than 75%, and very preferably more than 95% are 2-methylbutyl radicals. The aforementioned ranges are especially preferred when use is made, in accordance with the invention, of dialkyl terephthalates which have a total number of carbon atoms per alkyl radical of 5. With very particular preference the composition of the present invention contains a dialkyl terephthalate less than 0.5% by mass (based on the sum of the alkyl radicals), preferably less than 0.2%, and more preferably from 0.001 to 0.1% by mass of whose alkyl radicals are 3-methylbutyl radicals. The percentage distribution of the $C_5$ alkyl radicals can be easily ascertained by hydrolyzing the esters and separating off the resulting alcohol and subjecting it to analysis by gas chromatography (GC).

It can be advantageous if the composition of the present invention comprises, in addition to dialkyl terephthalate in which the alkyl radicals have a longest carbon chain of at least 4 carbon atoms and have a total number of carbon atoms per alkyl radical of 4 to 5, at least one further, primary plasticizer. By primary plasticizers are meant compounds which can be employed as sole plasticizers and which are compatible across wide concentration ranges with the polymer that is to be plasticized. The presence of primary plasticizers makes it possible to vary the properties of the composition of the invention. Besides the stated dialkyl terephthalates the composition of the present invention preferably comprises at least one further, primary plasticizer selected from dialkyl phthalates, trialkyl trimellitates, dialkyl adipates, dialkyl terephthalates, dialkyl 1,2-cyclohexanedicarboxylates, dialkyl 1,3 cyclohexanedicarboxylates, and dialkyl 1,4-cyclohexanedicarboxylates, with alkyl=alkyl radical having 7 to 11, especially 8 to 10, carbon atoms, glycol dibenzoates, and the alkylsulfonic esters of phenol, with alkyl=alkyl radical having from 8 to 22 carbon atoms, and acylated and nonacylated trialkyl citrates, polymeric plasticizers, and glycerol esters.

The fraction of primary plasticizers in the composition of the present invention is preferably from 20% to 99% by mass, based on the sum, contained in the composition, of primary plasticizers and dialkyl terephthalates in which the alkyl radicals have a longest carbon chain of at least 4 carbon atoms and a total number of carbon atoms per alkyl radical of 4 to 5, in particular 4 or 5. More preferably the fraction of primary plasticizers is from 25% to 80% and very preferably from 30% to 75% by mass.

It can be advantageous if the composition of the present invention comprises, besides dialkyl terephthalates in which the alkyl radicals have a longest carbon chain of at least 4 carbon atoms and have a total number of carbon atoms per alkyl radical of from 4 to 5, at least one alkyl benzoate where alkyl=alkyl radical having 8 to 10 carbon atoms, preferably nonyl benzoate or isononyl benzoate, and more preferably isononyl benzoate. The fraction of alkyl benzoate where alkyl=alkyl radical having 8 to 10 carbon atoms, particularly of isononyl benzoate, in the composition of the present invention is preferably from 5% to 90%, more preferably from 10% to 80%, and very preferably from 30% to 70% by mass, based on the sum, contained in the composition, of alkyl benzoates and alkyl terephthalates in which the alkyl radicals have a longest carbon chain of at least 4 carbon atoms and have a total number of carbon atoms per alkyl radical of from 4 to 5. The fraction of alkyl benzoate includes all values and subvalues therebetween, especially including 10, 15, 20, 25, 30, 35, 40, 45, 50, 55, 60, 65, 70, 75, 80 and 85% by mass.

It can be especially advantageous if compositions of the present invention comprise, besides dialkyl terephthalates in which the alkyl radicals have a longest carbon chain of at least 4 carbon atoms and have a total number of carbon atoms per alkyl radical of from 4 to 5, and at least one alkyl benzoate where alkyl=alkyl radical having 8 to 10 carbon atoms, at least one primary plasticizer. Such compositions of the present invention preferably have a fraction of dialkyl terephthalates having a total number of carbon atoms of from 4 to 5 per alkyl radical of from 5% to 70% by mass, a fraction of alkyl benzoate where alkyl=alkyl radical having 8 to 10 carbon atoms of from 5% to 70% by mass, and a fraction of primary plasticizers of from 20% to 90% by mass. The fraction of dialkyl terephthalates having a total number of carbon atoms of from 4 to 5 per alkyl radical includes all values and subvalues therebetween, especially including 10, 15, 20, 25, 30, 35, 40, 45, 50, 55, 60 and 65% by mass. The fraction of alkyl benzoate where alkyl=alkyl radical having 8 to 10 carbon atoms includes all values and subvalues therebetween, especially including 10, 15, 20, 25, 30, 35, 40, 45, 50, 55, 60 and 65% by mass. The fraction of primary plasticizers includes all values and subvalues therebetween, especially including 25, 30, 35, 40, 45, 50, 55, 60, 65, 70, 75, 80 and 85% by mass.

As well as the stated constituents, the composition of the present invention may contain further constituents, in particular, for example, further plasticizers, fillers, pigments, stabilizers, co-stabilizers such as epoxidized soybean oil, for example, lubricants, blowing agents, kickers, antioxidants or biocides. Further plasticizers which may be present in the compositions of the present invention include, in particular, esters of cyclohexanedicarboxylic acid, phthalic acid or adipic acid.

As representatives of the aforementioned polymers the composition of the present invention may comprise, in particular, polyacrylates having identical or different alkyl radicals of 4 to 10 carbon atoms, attached to the oxygen atom of the ester group, in particular with the n butyl, n hexyl, n-octyl, isononyl, and 2-ethylhexyl radical, poly methacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, methyl methacrylate-styrene-butadiene copolymers and/or nitrocellulose.

The polymer present in the compositions of the present invention may in particular be PVC. The composition of the present invention preferably contains suspension PVC, bulk PVC, microsuspension PVC or emulsion PVC as its PVC type.

The composition of the present invention may in particular be a plastisol, a synthetic leather, a floorcovering, an underbody sealant, a coated fabric, a sealing compound, a wallcovering, a varnish, a paint, an ink or an adhesive or may be used for producing these products.

The compositions of the present invention are preferably used to prepare plastisols, in particular to prepare PVC plastisols, having particularly advantageous processing properties. These plastisols may be used in numerous products, such as synthetic leather, floor coverings, wall coverings, etc., or to produce such products. Particular preference among these applications is given to use in cushion vinyl (CV) floor coverings, and in particular here in the top layer, where a further improvement in stain resistance is achieved. Use of the mixtures of the present invention as a formulation constituent can result in plastisols with low viscosity and increased storage stability and, at the same time, with accelerated gelling and improved low-temperature flexibilization. Preference is additionally given to their use in chemically or mechanically foamed layers or in compact layers and/or primers.

The terephthalic esters used in accordance with the present invention can be prepared from the corresponding alcohols or alcohol mixtures by reaction with terephthalic acid or derivatives thereof. In particular the terephthalic esters used in accordance with the present invention can be prepared either by esterification with terephthalic acid or, more preferably, by transesterification from terephthalic esters having shorter alcohol residues. In the case of transesterification a particularly preferred starting material is dimethyl terephthalate, an industrial mass product.

Alcohols for preparing the dialkyl terephthalates of the present invention may be any alcohols whose longest carbon chain is composed of 4 or 5 carbon atoms. Preference is given here to primary alcohols. Mention may be made here, by way of example of n-butanol, n-pentanol, 2-methylbutanol, and 3-methylbutanol, and also mixtures of these alcohols. Particular preference is given to using mixtures of n-pentanol and 2-methylbutanol in a mass ratio of from 99.9% to 70% pentanol and from 0.1% to 30% 2-methylbutanol. The amount of pentanol includes all values and subvalues therebetween, especially including 95, 90, 85, 80 and 75% by mass. The amount of 2-methylbutanol includes all values and subvalues therebetween, especially including 0.5, 1, 5, 10, 15, 20 and 25% by mass.

For preparing the dialkyl terephthalates of the present invention it is possible with preference to use primary alcohols or alcohol mixtures of the kind obtainable, for example, by hydroformylating an alkene with subsequent hydrogenation. Thus, for example, n-butanol can be prepared by hydroformylating propylene and subsequently hydrogenating the butyraldehyde to n-butanol. The isobutyraldehyde which is likewise produced in the hydroformylation of propylene can optionally be separated off by distillation.

Precursors of pentanols are preferably industrial hydrocarbon mixtures which contain one or more olefins having 4 carbon atoms. The major source of $C_4$ olefins is the $C_4$ cut of steamcracker petroleum. From this product, following (distillative) extraction of the butadiene or its selective hydrogenation to an n-butene mixture, a hydrocarbon mixture is produced (raffinate I or hydrogenated cracker $C_4$) that contains isobutene, 1-butene, and the two 2-butenes. Another feedstock for $C_4$ olefins is the $C_4$ cut from FCC plants, which can be worked up in the way described above. $C_4$ olefins produced by Fischer-Tropsch synthesis are likewise a suitable feedstock, following selective hydrogenation of the butadiene they contain to n-butenes. Furthermore, olefin mixtures obtained by dehydrogenation of $C_4$ hydrocarbons or by metathesis reactions, or other industrial olefin streams, may be suitable feedstocks. Precursors for the pentanols, in addition to raffinate I, include raffinate II, raffinate III—a stream obtained by separating off the major part of 1-butene from raffinate II—and what is called crude butane, which is obtained following an oligomerization of raffinate II and which in addition to alkanes has as its only olefin small amounts of 2-butene. The advantage of using raffinate II, raffinate III or crude butane as a pentanols precursor is that they include no isobutene, or virtually no isobutene, and so the resulting pentanols include only very small amounts (less than 0.5% by mass relative to the pentanols) of 3-methylbutanol, or none at all.

Owing to the level of effort required to separate the feedstock mixtures, which is frequently very high, it can be advantageous not to separate out the olefins present in the industrial mixture to be used as the feedstock mixture, but instead to use the mixtures directly.

With particular preference the dialkyl terephthalates used in accordance with the present invention are prepared by a process for preparing dialkyl terephthalates whose alkyl radicals have a longest carbon chain or at least 4 carbon atoms and have a total number of carbon atoms per alkyl radical of from 4 to 5, comprising the steps of
  a) hydroformylating $C_3$ or $C_4$ olefins to give $C_4$ or $C_5$ aldehydes, respectively,
  b) hydrogenating the aldehydes obtained in step a) to the corresponding alcohols, and
  c) reacting the alcohols from b) with terephthalic acid or with a derivative of terephthalic acid to the corresponding diester.

It can be advantageous if after step a) (hydroformylation) and/or b) (hydrogenation) of the process the product mixtures obtained in these process stages are separated out into the individual isomers. Such separation may take place thermally, for example, in particular by means of distillation.

Process Step a)

The hydroformylation of all the olefins in the feedstock mixture can take place in one stage. This may be advantageous particularly when, in the case of propene hydroformylation, there is only one olefinic compound in the feedstock mixture. The hydroformylation of feedstock mixtures containing propene as sole olefin can be carried out in one stage under the conditions described below for the first stage and using the catalyst described there.

Where pentanols are to be prepared, isomerically pure butenes, such as 1-butene, 2-butene, and isobutene, for example, can likewise be used in step a) of the process. Since, however, the feedstock mixtures frequently do not contain isomerically pure olefins but instead contain usually industrial mixtures of $C_4$ hydrocarbons, as have been described above, step a) of the process of the present invention with preference uses a mixture of olefins which contains isobutene and/or 1-butene and 2-butenes.

The hydroformylation of the olefins present in the feedstock mixture may in turn take place in one stage. For this purpose it is preferred to use a catalyst having the ability to hydroformylate olefins with different double-bond position and/or different numbers of branching sites. However, catalysts suitable for that purpose usually produce only a low selectivity for the formation of products (aldehydes, alcohols, formates) which have come about through terminal hydroformylation, and/or exhibit a reaction rate which is too low for an industrial process.

If the aim is to obtain feedstock alcohols, especially pentanols or pentanol mixtures with a very low degree of branching, from the hydroformylation products, it is advantageous to carry out the hydroformylation in such a way as to produce a high proportion of products which have come about through terminal hydroformylation, since only the terminally hydroformylated products have the same degree of branching as their parent olefins; with internal hydroformylation, in contrast, the degree of branching of the resulting product is increased by 1.

The olefins present in an industrial mixture differ considerably in terms of their hydroformylation reactivity. Generally speaking, olefins with terminal double bonds are more reactive than olefins with internal double bonds, and linear olefins are more reactive than their branched counterparts. For the case of the $C_4$ olefins specifically, 1-butene is more reactive than isobutene, and isobutene is more reactive than the two 2-butenes (cis and trans). This difference in reactivity can be utilized in order to produce a high proportion of products which have come about through terminal hydroformylation; in other words, 1-butene should be converted principally into valeraldehyde and not 2-methylbutanal, isobutene should be converted into 3-methylbutanal and not 2,2-dimethylpropanal, and the two 2-butenes should form a very large proportion of valeraldehyde (n-pentanal) and little 2-methylbutanal.

Since there is as yet no catalyst which simultaneously effects not only the reaction of 1-butene but also that of isobutene and the 2-butenes at satisfactory rate to products which have come about through terminal hydroformylation, the hydroformylation is carried out—especially if the feedstock mixtures contain not only isobutene and/or 1 butene but also 2-butenes—in at least two stages. Where the process of the present invention is carried out in two stages, it is preferred to hydroformylate isobutene and/or 1-butene in one stage and 2-butenes in the other stage.

In a first stage the hydroformylation is preferably performed with a suitable catalyst under conditions under which only α-olefins (1-butene, isobutene), but not the 2-butenes, are converted to the corresponding aldehydes. In this stage, the conditions are selected preferably such that 1-butene is converted as selectively as possible into valeraldehyde and isobutene is converted as selectively as possible into 3-methylbutanal. Catalysts which can be used include, for example, compounds containing rhodium and triorganic phosphorus compounds, especially phosphines, as ligands. The reaction can be carried out in a homogeneous phase (in analogy to the UCC process, described in EP 0 562 451) or in a heterogeneous phase (in analogy to the Rhone-Poulenc-Ruhrchemie process, described in DE 026 27 354 and EP 0 562 451). Owing to the greater ease with which the catalyst can be separated off, the first stage of step a) of the process is preferably carried out by the second process. The reaction temperatures for the first stage of process step a) are preferably from 70 to 150° C., more preferably from 100 to 130° C. The process pressures are preferably from 2 to 20 MPa, more preferably from 3 to 6 MPa. The reaction temperature includes all values and subvalues therebetween, especially including 75, 80, 85, 90, 95, 100, 105, 110, 115, 120, 125, 130, 135, 140 and 145° C. The pressure includes all values and subvalues therebetween, especially including 5, 10, 15 MPa.

The hydroformylation of the 1-olefins can optionally be carried out in a multiphase system, with the reactant, product, and synthesis gas in dispersion in a continuous catalyst phase, at high superficial velocities. Such processes are described in, for example, DE 199 25 384 A1 and DE 199 57 528 A1, which are hereby expressly incorporated by reference.

The hydroformylation of the 1-olefins in the first stage of process step a) can be carried out in one or two stages. In the case of two-stage hydroformylation, 1-butene is converted predominantly in the first reactor and isobutene primarily in the second. In the two reactors the same catalysts or different catalysts can be used. If the same catalysts are used a joint catalyst workup procedure is possible.

At the end of the hydroformylation of 1-butene and parts of the isobutene in the first stage of process step a), as just described, the feedstock hydrocarbon mixture still contains the 2 butenes (if present) and, where appropriate, isobutene, and no more than traces of 1 butene. This mixture can be hydroformylated as it is using a different catalyst system, or can be hydroformylated only after it has been separated into two fractions, of which one contains isobutene and the other contains the two 2-butenes. Preferably the mixture is separated, and the isobutene-containing fraction and 2-butene-containing fraction are hydroformylated separately.

The isobutene, or isobutene-containing fraction, can be hydroformylated to 3-methylbutanal with high selectivities. Suitable catalysts for this conversion are rhodium complexes containing monodentate or polydentate phosphite ligands. Examples of suitable monodentate phosphite ligands include triarylphosphites whose aryl groups not only have a bulky group positioned ortho to the phosphite oxygen but are also substituted in meta or para position, such as tris(2,4-di-tert-butylphenyl)phosphite. The hydroformylation of isobutene using a catalyst system composed of rhodium and a bisphosphite is described in, for example, U.S. Pat. Nos. 4,668,651, 4,769,498 and WO 85/03702, which are hereby expressly incorporated by reference to form part of the disclosure content of the present description.

An option is to recycle some or all of the isolated isobutene fraction to the preceding, first hydroformylation stage. In that case it may be particularly advantageous to separate off the saturated hydrocarbons from the isobutene, which can be accomplished thermally, for example. Following such removal of the saturated hydrocarbons it may be particularly advantageous to recycle all of the isobutene to the preceding, first hydroformylation stage.

The hydroformylation of 2-butenes or 2-butene-containing fractions can be carried out by means of a variety of known catalysts, and usually produces a mixture of 2-methylbutanal and valeraldehyde. In the majority of cases 2-methylbutanal is the principal product. The use of unmodified cobalt catalysts for the hydroformylation of 2-butenes is described in EP 0 646 563, that of unmodified rhodium in EP 0 562 451. In addition it is possible to use the same catalyst system for hydroformylating 2-butenes as for hydroformylating isobutene: that is, a complex of rhodium and monodentate triaryl phosphite. High selectivities to valeraldehyde can be obtained when using a catalyst composed of rhodium and bulky aromatic bisphosphites, of the kind described in, for example, EP 0 213 639, EP 0 214 622 or U.S. Pat. No. 5,763,680. However, for an industrial process the reaction rates are relatively low. Particular preference is given to using a bisphosphite ligand of the type identified as ligand D in U.S. Pat. No. 5,763,680.

As remarked above, the olefins present in the feedstock may be hydroformylated separately or jointly. If no great importance is attached to the linearity of the end products, it is advantageous to hydroformylate the olefins jointly. If, in contrast, an end product with very little branching is desired, it is preferred to carry out the hydroformylation in at least two stages. In the case of a $C_4$ olefin mixture, the latter case implies that 1-butene and, where appropriate, isobutene are reacted in the first reactor and the remaining olefins, optionally, in the downstream reactor(s).

The catalyst can be separated off from the hydroformylation mixtures by known methods. In the case of processes where the rhodium catalyst is present homogeneously in the reaction mixture, for example, the catalyst can be separated off by distillation. In the case of reaction in a heterogeneous phase (two liquid phases) the catalyst can be separated off by means, for example, of phase separation (B. Cornils, W. A. Herrmann (Eds.), Applied Homogeneous Catalysis with Organic Compounds, Vol. 1, p. 80, VCH-Verlag, 1996).

Process Step b)

Following catalyst removal, the hydroformylation mixtures can either be used directly in the hydrogenation or else separated beforehand into two or more fractions by distillation or by other separation methods. In particular it may be advantageous to work up the hydroformylation mixture so as to give one or more fractions containing substantially aldehydes.

The decatalyzed hydroformylation mixtures, or the aldehydes or aldehyde-containing fractions separated off from them by a separation method such as distillation, for example, are hydrogenated in accordance with the invention. The hydroformylation mixtures can be hydrogenated separately or jointly. Hydrogenation forms the corresponding saturated alcohols from the aldehydes. These alcohols are, for example, butanols, n-pentanol, and 2-methylbutanol and 3-methylbutanol.

The hydrogenation can be carried out using, for example, nickel, copper, copper/nickel, copper/chromium, copper/chromium/nickel, zinc/chromium or nickel/molybdenum catalysts. The catalysts may be unsupported, or the actively hydrogenating substances and/or their precursors may have been applied to supports, such as silica or alumina, for example. Preferred catalysts which can be used in process step b), and over which the hydroformylation mixtures can be hydrogenated, contain from 0.3% to 15% by mass each of copper and nickel and as activators from 0.05% to 3.5% by mass of chromium, and optionally from 0.01% to 1.6% by mass, preferably from 0.02% to 1.2% by mass, of an alkali metal component on a support material, preferably alumina and silica. The amount of copper and nickel includes all values and subvalues therebetween, especially including 0.5, 1, 5 and 10% by mass. The amount of activator includes all values and subvalues therebetween, especially including 0.1, 0.5, 1, 1.5, 2, 2.5, and 3% by mass. The amount of alkali metal component on a support material includes all values and subvalues therebetween, especially including 0.05, 0.1, 0.5, 1 and 1.5% by mass. The amounts are based on the catalyst prior to reduction. The alkali metal component is optional. The catalysts are used advantageously in a form in which they present little flow resistance such as in the form of granules, pellets or shaped bodies, such as tablets, cylinders, extrudates or rings. They are advantageously activated before being used, by means of heating in a stream of hydrogen, for example.

The hydrogenation may be a gas-phase or liquid-phase hydrogenation. The hydrogenation is carried out preferably under an overall pressure of from 0.5 to 50 MPa, more preferably from 1.5 to 10 MPa. The pressure includes all values and subvalues therebetween, especially including 1, 5, 10, 15, 20, 25, 30, 35, 40 and 45 MPa. Hydrogenation in the gas phase may also be carried out at lower pressures, in which case correspondingly large volumes of gas are present. Where two or more hydrogenation reactors are employed, the overall pressures in the individual reactors may be the same or different within the stated pressure limits. In the case of hydrogenation in liquid phase or gaseous phase, the reaction temperatures can amount generally to from 120 to 220° C., in particular from 140 to 180° C. The temperature includes all values and subvalues therebetween, especially including 125, 130, 135, 140, 145, 150, 155, 160, 165, 170, 175, 180, 185, 190, 195, 200, 205, 210 and 215° C. Such hydrogenations are described in, for example, patent applications DE 198 42 369 and DE 198 42 370, hereby expressly incorporated by reference.

The hydrogenation is carried out preferably in the presence of water. The water required may be present in the feed to the reactor. It is, however, also possible to insert water into the hydrogenation apparatus at a suitable point. In the case of gas-phase hydrogenation water is supplied advantageously in the form of steam. One preferred hydrogenation process is that of liquid-phase hydrogenation with the addition of water, as described in DE 100 62 448, for example. Particular preference is given to carrying out hydrogenation with a water content of from 0.05 to 10% by mass, in particular from 0.5 to 5% by mass, very particularly from 1% to 2.5% by mass. The water content includes all values and subvalues therebetween, especially including 0.1, 0.5, 1, 2, 4, 6, and 8% by mass. The water content here is determined in the hydrogenation discharge.

The mixtures obtained from the hydrogenation can either be used directly in the esterification or transesterification stage or else separated into two or more fractions by distillation or using other separation methods. In particular it can be advantageous to workup the hydrogenation mixture in such a way as to give one or more fractions of alcohols having the same number of carbon atoms. The distillative workup can be carried out preferably such that there is substantial separation into the individual constituents.

If a terephthalic ester of linear feedstock alcohols is to be prepared, then the linear alcohols, such as n-pentanol, can be separated off from the branched alcohols, such as branched pentanols, by distillation.

Process Step c)

The conversion of the feedstock alcohols obtained in process step b) into the corresponding diester can be accomplished by reaction with terephthalic acid or with a derivative of terephthalic acid, in particular a terephthalic ester. In process step c) it is preferred to carry out esterification of terephthalic acid or transesterification of dimethyl terephthalate with the alcohol obtained from step b).

The terephthalic esters of the present invention can be obtained by, for example, esterifying terephthalic acid with the corresponding alcohols. The alcohol or alcohol mixture which is used to form the ester, and which at the same time may serve as an azeotrope former for separating off the water formed in the reaction, is used preferably in excess, more preferably with an excess of from 5% to 50%, in particular from 10% to 30%, of the molar amount required to form the ester.

In the case of esterification with butanols or pentanols, or with butanol or pentanol mixtures, the reaction under atmospheric pressure is relatively slow, owing to the high melting point of the terephthalic acid and the comparatively poor solubility of terephthalic acid in these alcohols, since the temperature can be raised only slightly above the boiling point of the alcohols or alcohol mixture. To increase the rate of esterification it may therefore be advantageous to carry out the reaction at an increased pressure and hence also at an elevated reaction temperature. The reaction can also be carried out optionally with an initial deficit of alcohol. In this case the full amount of alcohol (including the preferred excess where appropriate) is added only in the course of the reaction, slowly.

Esterification catalysts used can be acids, such as sulfuric acid, methanesulfonic acid or p-toluenesulfonic acid, for example, or metals or compounds thereof. Suitable examples include tin, titanium, and zirconium, which may be used as finely divided metals or, advantageously, in the form of their salts, oxides or soluble organic compounds. The metal catalysts are high-temperature catalysts as compared with the catalysts based on protic acids, and often attain their full activity only at temperatures above 180° C. It can be advantageous to use metal catalysts of this kind based on metals or compounds thereof, since it has been found that with these catalysts, in comparison to catalysts based on protic acids, the level of by-products formed is lower—olefins from the alcohol employed, for example. Exemplary representatives of metal catalysts employed with particular preference are tin powder, tin(II) oxide, tin(II) oxalate, titanic esters such as tetraisopropyl orthotitanate or tetrabutyl orthotitanate, and zirconium esters such as tetrabutyl zirconate.

The catalyst concentration can be varied in wide ranges and in particular can be varied as a function of the type of catalyst. In the case of the titanium compounds used with preference, the catalyst concentration is preferably from 0.005% to 1.0% by mass, based on the reaction mixture, more preferably from 0.01% to 0.5% by mass, and very preferably from 0.01% to 0.1% by mass. The catalyst concentration includes all values and subvalues therebetween, especially including 0.01, 0.05, 0.1, 0.2, 0.3, 0.4, 0.5, 0.6, 0.7, 0.8 and 0.9% by mass.

The reaction temperatures when using catalysts based on titanium or compounds of titanium is preferably from 160° C. to 270° C., more preferably from 180 to 250° C. The temperature includes all values and subvalues therebetween, especially including 170, 180, 190, 200, 210, 220, 230, 240, 250 and 260° C.

In general the optimum temperatures for carrying out the esterification depend on the feedstock, on the progress of the reaction, and on the catalyst concentration. The optimum temperatures for each individual case can be readily determined by means of simple preliminary tests. Through the use of higher temperatures it is possible to increase the reaction rate, although this does favor side reactions, such as elimination of water from alcohols, or formation of colored byproducts, for example.

The desired reaction temperature or the desired temperature range can be set by adapting the pressure in the reaction vessel. In the case of low-boiling alcohols, therefore, the reaction is carried out preferably at overpressure and in the case of higher-boiling alcohols preferably under reduced pressure. In the present case, therefore, the esterification is carried out preferably at an overpressure, more preferably at an overpressure of 2 to 8 bar.

To remove the water of reaction it can be advantageous if the water is removed as an azeotropic mixture with the alcohol by distillation from the reaction mixture. The volume of liquid to be supplied to the reaction may be composed in whole or in part of alcohol recovered by working up the azeotropic distillate. It is also possible to carry out the workup at a later point in time and to replace some or all of the liquid volume removed by fresh alcohol, i.e., an alcohol held ready in a stock vessel.

The crude ester mixtures, which besides the ester(s) contain alcohol, catalyst or its follow-on products, and, where appropriate, byproducts, can be worked up by methods which are known per se. Workup preferably comprises the following steps: separating off the excess alcohol and any low boilers, neutralizing the acids present, optionally performing steam distillation, converting the catalyst into a readily filterable residue, separating off the solids, and, where appropriate, drying. The sequence of these steps may differ according to the specific workup method employed.

The desired ester, dialkyl ester, or mixture of esters from the reaction mixture, where appropriate following neutralization of the batch, can optionally be separated off or fractionated by distillation. This may be advantageous particularly in the case of products which are solid at room temperature, such as di-3-methylbutyl terephthalate, for example.

In another embodiment of the process of the present invention the terephthalic esters of the present invention can be obtained by transesterifying a dialkyl terephthalate with a feedstock alcohol selected from butanol, pentanol or a suitable pentanol isomer mixture. Reactants used are dialkyl terephthalates whose alkyl radicals attached to the oxygen atom of the ester group contain 1 to 3 carbon atoms. These radicals may be aliphatic, linear or branched, alicyclic or aromatic. One or more methylene groups in these alkyl radicals may be substituted by oxygen. It can be advantageous if the boiling point of the alcohols on which the reactant ester is based are lower than those of the feedstock alcohols. One preferred feedstock is dimethyl terephthalate (DMT), which is produced industrially and is therefore available in large quantities.

The transesterification can for example be/is carried out catalytically, using Brønsted or Lewis acid or base catalysts for example. Irrespective of which catalyst is employed, a temperature-dependent equilibrium is always developed between the feedstocks (dialkyl terephthalate and feedstock alcohols) and the products (inventive terephthalic ester and liberated alcohol from the feedstock dialkyl terephthalate). In order to shift the equilibrium in favor of the inventive terephthalic ester it can be advantageous to remove the alcohol generated by the reactant ester from the reaction mixture by distillation.

With this embodiment of the process of the present invention as well it can be advantageous to use the alcohol in excess overall. The feedstock alcohol is used preferably in an excess of from 5% to 50%, in particular from 10% to 30%, of the molar amount required to form the dialkyl terephthalate of the invention.

Transesterification catalysts used can be acids, such as sulfuric acid, methanesulfonic acid or p-toluenesulfonic acid, for example, or metals or compounds thereof. Suitable examples of metals or compounds thereof include tin, titanium, and zirconium, which are used as finely divided metals or, advantageously, in the form of their salts, oxides or soluble organic compounds. The metal catalysts are high-temperature catalysts as compared with the catalysts based on protic acids, and often attain their full activity only at temperatures above 180° C. It can be advantageous to use metal catalysts of this kind based on metals or compounds thereof, since it has been found that with these catalysts, in comparison to catalysts based on protic acids, the level of by-products formed is lower—olefins from the alcohol employed, for example. Exemplary representatives of metal catalysts employed with particular preference are tin powder, tin(II) oxide, tin(II) oxalate, titanic esters such as tetraisopropyl orthotitanate or tetrabutyl orthotitanate, and zirconium esters such as tetrabutyl zirconate. Furthermore, it is possible to use basic catalysts, such as oxides, hydroxides, hydrogen carbonates, carbonates or alkoxides of alkali metals or alkaline earth metals, for example. From this group it is preferred to use alkoxides, such as sodium methoxide, for example. Alkoxides can also be prepared in situ from an alkali metal and a nonanol or an isononanol mixture. Particular preference is given to using alkoxides whose alcohol residue matches one of the alcohols involved in the reaction.

The catalyst concentration can be varied in wide ranges and can be varied in particular as a function of the type of catalyst. The catalyst concentration is preferably from 0.005% to 1.0% by mass, based on the reaction mixture. The catalyst concentration includes all values and subvalues therebetween, especially including 0.01, 0.05, 0.1, 0.2, 0.3, 0.4, 0.5, 0.6, 0.7, 0.8 and 0.9% by mass. The optimum concentrations for each catalyst can be readily determined by means of preliminary tests, and result from a tradeoff between minimal catalyst consumption (i.e., costs) and maximum reaction rate. In the case of the particularly preferred tetrabutyl orthotitanate the preferred concentration, for example, is in the range from 0.05% to 1% by mass, based on the dialkyl terephthalate employed.

The transesterification is carried out preferably at a temperature from 100 to 220° C. The temperature includes all values and subvalues therebetween, especially including 110, 115, 120, 125, 130, 135, 140, 145, 150, 155, 160, 165, 170, 175, 180, 185, 190, 195, 200, 205, 210 and 215° C. The temperature level selected is with particular preference such that the alcohol formed from the reactant ester can be removed from the reaction mixture by distillation under the prevailing pressure, preferably elevated pressure.

Because of the low boiling points of the alcohols (butanols or pentanols) used for the transesterification it can be advantageous, in order to attain a temperature sufficient for catalysis with metal catalysts such as tetrabutyl orthotitanate, to carry out the reaction either under increased pressure or, initially, with a markedly substoichiometric proportion of feedstock alcohol. Otherwise, below this temperature, the transesterification proceeds only at a very moderate rate.

If the reaction is carried out with a substoichiometric proportion of feedstock alcohol to start with, then it has proven advantageous if, after the target temperature has been reached, the remaining alcohol is added at a slow rate such that the temperature of the reaction mixture, measured in the liquid phase, does not fall below said target temperature. The preferred target temperature in the case of the transesterification of DMT with butanol or pentanols or pentanol mixtures is at least 160° C., preferably more than 180° C.

The transesterification mixtures can be worked up in exactly the same way as described for the esterification mixtures.

Having generally described this invention, a further understanding can be obtained by reference to certain specific examples which are provided herein for purposes of illustration only, and are not intended to be limiting unless otherwise specified.

EXAMPLES

Example 1

Preparation of di-n-pentyl terephthalate

A 2-liter multineck flask with distillation bridge and reflux divider, 20 cm packed column, stirrer, dip tube, dropping funnel, and thermometer was charged with 679 g (3.5 mol) of dimethyl terephthalate (Oxxynova), 1.7 g of tetrabutyl orthotitanate (0.25% by mass based on DMT, DuPont, Tyzor TnBT) and, to start with, 200 g out of a total of 748 g (8.5 mol)

of n-pentanol (>99% purity, FLUKA), and this initial charge was heated slowly until the DMT forms a homogeneous mixture with the alcohol, at which point the stirrer was switched on. The reflux divider was set so that the overhead temperature remained at a constant level of approximately 65° C. (the boiling point of methanol). From a liquid-phase temperature of approximately 185° C., the remaining alcohol was slowly run in at a rate such that the temperature in the flask did not fall below 180° C. and a reflux sufficient for the distillation was maintained. The distillate removed was analyzed by GC for the amount of methanol separated off. After a major fraction of the methanol (approximately 90% of the anticipated 7 mol of methanol) had been taken off, a sample was taken from the reaction flask every 30 minutes and analyzed by GC. Transesterification was at an end when the amount of dimethyl ester and mixed ester(methyl pentyl) in total had dropped below 0.3% by mass (approximately 8 to 9 hours).

For working up, the reflux divider was opened up completely and reduced pressure (approximately 800 to 5 hPa) was carefully applied until the excess of alcohol had been distilled off. This was followed by cooling to 80° C. and nitrogen blanketing of the apparatus. The acid number of the flask contents was measured in accordance with DIN EN ISO 2114 and said contents were stirred at 80° C. for 30 minutes with three times the stoichiometric amount (in relation to the acid number) of 10% strength by mass aqueous sodium hydroxide solution. Subsequently it was heated to 160° C. and an underpressure of approximately 5 to 30 hPa was applied, at which point water (8% by mass based on flask contents) was carefully added dropwise via the dropping funnel. By means of this procedure (cf. steam distillation) further low boilers were separated off. Thereafter the heating was shut off and the product was dried under a pressure of approximately 5 hPa. When the temperature had dropped below 100° C., the product was filtered via a suction filter with filter paper and filtration aid (perlite).

Example 2

Preparation of di-n-butyl terephthalate

A 2-liter multineck flask with distillation bridge and reflux divider, 20 cm packed column, stirrer, dip tube, dropping funnel, and thermometer was charged with 679 g (3.5 mol) of dimethyl terephthalate (Oxxynova), 1.7 g of tetrabutyl orthotitanate (0.25% by mass based on DMT, DuPont, Tyzor TnBT) and, to start with, 200 g out of a total of 629 g (8.5 mol) of n-butanol (European Oxo, purity 99.9%), and this initial charge was heated slowly until the DMT forms a homogeneous mixture with the alcohol, at which point the stirrer was switched on. The reflux divider was set so that the overhead temperature remained at a constant level of approximately 65° C. (the boiling point of methanol). From a liquid-phase temperature of approximately 185° C., the remaining alcohol was slowly run in at a rate such that the temperature in the flask did not fall below 180° C. and a proper reflux was maintained. The distillate removed was analyzed by GC for the amount of methanol separated off. After a major fraction of the methanol (approximately 90% of the anticipated 7 mol of methanol) had been taken off, a sample was taken from the reaction flask every 30 minutes and analyzed by GC. Transesterification was at an end when the amount of dimethyl ester and mixed ester(methyl butyl) in total had dropped below 0.3% (after approximately 8 to 9 hours).

For working up, the reflux divider was opened up completely and reduced pressure (approximately 800 to 5 hPa) was carefully applied until the excess of alcohol had been distilled off. This was followed by cooling to 80° C. and nitrogen blanketing of the apparatus. The acid number of the flask contents was measured in accordance with DIN EN ISO 2114 and said contents were stirred at 80° C. for 30 minutes with three times the stoichiometric amount (in relation to the acid number) of 10% strength by mass aqueous sodium hydroxide solution. Subsequently it was heated to 160° C. and an underpressure of approximately 5 to 30 hPa was applied, at which point water (8% by mass based on flask contents) was carefully added dropwise via the dropping funnel. By means of this procedure (cf. steam distillation) further low boilers were separated off. Thereafter the heating was shut off and the product was dried under a pressure of approximately 5 hPa. When the temperature had dropped below 100° C., the product was filtered via a suction filter with filter paper and filtration aid (perlite).

Example 3

Preparation of Plastisols

The initial masses of the components used for the various plastisols 1 to 3 are apparent from Table 1 below.

TABLE 1

Formulas (all amounts in phr (i.e., parts by mass per 100 parts by mass of PVC))

|  | Plastisol 1 (comparative) | Plastisol 2 (inventive) | Plastisol 3 (inventive) |
| --- | --- | --- | --- |
| Vestolit B 7021 (Vestolit) | 100 | 100 | 100 |
| Vestinol 9 (OXENO) | 30 | 30 | 30 |
| Diisobutyl phthalate (Palatinol IC, BASF) | 20 |  |  |
| Di-n-butyl terephthalate |  | 20 |  |
| Di-n-pentyl terephthalate |  |  | 20 |
| Epoxidized soybean oil | 3 | 3 | 3 |
| Mark CZ 140 | 1.5 | 1.5 | 1.5 |

The plasticizers were conditioned to a temperature of 25° C. before being added. First of all the liquid constituents and then the pulverulent constituents were weighed out into a PE beaker. The mixture was stirred in by hand using a paste spatula so that none of the powder remained unwetted. The mixing beaker was then clamped into the clamping apparatus of a dissolver stirrer. Prior to immersion of the stirrer into the mixture, the rotary speed was set at 1800 revolutions per minute. After the stirrer had been switched on, stirring was continued until the temperature on the digital display of the temperature sensor reached 30.0° C. This ensured that homogenization of the plastisol was achieved with a defined energy input. Thereafter the temperature of the plastisol was immediately controlled to 25.0° C.

Example 4

Measurement of Plastisol Viscosities and of Storage Stability

The viscosities of the plastisols prepared in Example 3 were measured as follows by a method based on DIN 53 019, using the Physica DSR 4000 rheometer (Paar-Physica), which was controlled by the associated US 200 software.

The plastisol was again stirred with a spatula in the stock vessel and was subjected to measurement in the Z3 measurement system (DIN 25 mm) in accordance with the operating instructions. The measurement ran automatically at 25° C. via the abovementioned software. The settings were as follows:
pre-shear of 100 s-1 for a period of 60 s, during which no values were measured
downward progression beginning at 200 s-1 and ending at 0.1 s-1, divided into a logarithmic series with 30 steps, the duration of each point of measurement being 5 s.

After the measurement, the data were processed automatically by the software. The viscosity was plotted as a function of the shear rate. Each of the measurements was made after 2 h and 7 d. Between these junctures, the paste was stored at 25° C.

Table 2 below lists the viscosity values obtained for the shear rate of 118 s-1 after each of the indicated storage times.

TABLE 2

Shear rate 118 s-1 (viscosity data in Pa * s)

| | Plastisol | | |
|---|---|---|---|
| | 1 | 2 | 3 |
| 2 h | 6.1 | 4.6 | 4.1 |
| 7 d | 14.6 | 9.6 | 8.0 |
| Increase by a factor of | 2.4 | 2.1 | 2 |

The viscosities of the two inventive plastisols were situated at a lower level than that of the comparative example. Moreover, the relative increase in viscosity was much lower for the inventive examples, and the storage stability, accordingly, was higher.

Example 5

Measurement of Gelling Performance

The gelling performance of the plastisols was investigated in a Bohlin CVO oscillation viscometer (measurement system PP20) operated with shear stress control.
The following parameters were set:
Mode: Temperature gradient
Start temperature: 25° C.
End temperature: 180° C.
Heating/cooling rate: 2° C./min
Temperature after measurement: 25° C.
Oscillation frequency: 2 Hz
Delay time: 1 s
Waiting time: 15 s
Continuous oscillation: on
Automatic shear stress preset: on
Shear stress at start: 0.3 Pa
Required deformation: 0.002
Gap width: 0.5 mm
Measurement Procedure:
A spatula was used to apply a drop of the test plastisol (formulas), free from air bubbles, to the lower plate of the measurement system. Care was taken here to ensure that some plastisol was able to exude uniformly out of the measurement system (not more than about 6 mm overall) after the system had been closed. The protective covering, which also serves for thermal insulation, was then fitted, and the measurement commenced.

The "complex viscosity" of the plastisol was plotted as a function of the temperature. The onset of gelling was apparent from a sudden marked rise in complex viscosity. The earlier the onset of this viscosity rise, the better the gelling capability of the system.

FIG. 1 shows the section of the viscosity/temperature curve ("gelling curve") which was relevant for the onset of gelling in the measurements carried out in Example 5. The Y axis shows the complex viscosities in Pa·s, the X axis the temperatures in ° C. The gelling curve for plastisol 1 is depicted as a continuous line, with diamonds showing the individual values. The gelling curve for plastisol 2 is shown as a dashed line, with squares showing the individual values. The gelling curve for plastisol 3 is depicted as a dotted line, with circles showing the individual values.

Compared to the comparative example (plastisol 1), the inventive plastisol 2 exhibited substantially improved gelling, which was manifested by the onset of the rise in the curve being situated at lower temperatures. The likewise inventive plastisol 3 was classed as approximately equivalent to plastisol 1 in terms of gelling properties, within the bounds of measurement accuracy.

It is clear overall that the inventive plasticizers and the inventive plastisols prepared from them exhibit a very good profile of properties.

German patent application 10 2006 001 795.1 filed Jan. 12, 2006, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:
1. A plasticizer composition, comprising:
dialkyl terephthalate,
wherein the alkyl radicals of said dialkyl terephthalate have a longest carbon chain of at least 4 carbon atoms and have a total number of carbon atoms per alkyl radical of 5; and
at least one primary plasticizer selected from the group consisting of phthalic acid dialkyl esters, trimellitic acid trialkyl esters, adipic acid dialkyl esters, 1,2-cyclohexanedioic acid alkyl esters, 1,3-cyclohexanedioic acid alkyl esters with alkyl=alkyl radical having 8 to 10 carbon atoms, 1,4-cyclohexanedioic acid alkyl esters with alkyl=alkyl radical having 8 to 10 carbon atoms, glycol dibenzoates, alkylsulphonic esters of phenol with alkyl=alkyl radical having 8 to 22 carbon atoms, acylated citric acid trialkyl esters, non-acylated citric acid trialkyl esters, polymer plasticizers, glycerol esters and mixtures thereof, with the proviso that the primary plasticizer is not dioctyl phthalate, isononyl benzoate or dioctyl terephthalates; and
wherein from 85% to 98% of the alkyl radicals of said dialkyl terephthalate are n-pentyl radicals and from 15% to 2% are methylbutyl radicals.

2. The plasticizer composition according to claim 1, wherein the fraction of primary plasticizers is from 20% to 99% by mass.

3. The plasticizer composition according to claim 1, further comprising at least one alkyl benzoate where alkyl=alkyl radical having from 7 to 13 carbon atoms.

4. A composition, comprising:
the plasticizer composition of claim 1; and
a polymer selected from the group consisting of PVC, PVB, PAMA, homopolymers or copolymers based on ethylene, propylene, butadiene, vinyl acetate, glycidyl acrylate, glycidyl methacrylate, methacrylates, acrylates, acrylates or methacrylates in which attached to the oxygen atom of the ester group there are alkyl radicals of branched or unbranched alcohols having from one to ten carbon atoms, styrene, acrylonitrile, cyclic olefins and mixtures thereof.

5. The composition according to claim 4, comprising suspension PVC, bulk PVC, microsuspension PVC or emulsion PVC.

6. The composition according to claim 4, comprising further plasticizers, fillers, pigments, stabilizers, lubricants, blowing agents, kickers, antioxidants or biocides.

7. The composition according to claim 4, which is a plastisol, a synthetic leather, a floorcovering, an underbody sealant, a coated fabric, a wallcovering, a varnish, a paint, a sealing compound, an ink or an adhesive.

8. A plasticizer, comprising:
the composition of claim 4.

9. An adhesive, comprising:
the composition of claim 1.

10. A sealing composition, comprising:
the composition of claim 1.

11. A paint, comprising:
the composition of claim 1.

12. An ink, comprising:
the composition of claim 1.

13. A plasticizer composition, comprising:
dialkyl terephthalate,
wherein the alkyl radicals of said dialkyl terephthalate have a longest carbon chain of at least 4 carbon atoms and have a total number of carbon atoms per alkyl radical of 5; and
at least one primary plasticizer selected from the group consisting of phthalic acid dialkyl esters, trimellitic acid trialkyl esters, adipic acid dialkyl esters, terephthalic acid dialkyl esters, 1,2-cyclohexanedioic acid alkyl esters, 1,3-cyclohexanedioic acid alkyl esters with alkyl=alkyl radical having 8 to 10 carbon atoms, 1,4-cyclohexanedioic acid alkyl esters with alkyl=alkyl radical having 8 to 10 carbon atoms, glycol dibenzoates, alkylsulphonic esters of phenol with alkyl=alkyl radical having 8 to 22 carbon atoms, acylated citric acid trialkyl esters, non-acylated citric acid trialkyl esters, polymer plasticizers, glycerol esters and mixtures thereof;
wherein when said dialkyl terephthalates and said phthalic acid dialkyl esters are used together they are different from each other; and
wherein from 85% to 98% of the alkyl radicals of said dialkyl terephthalate are n-pentyl radicals and from 15% to 2% are methylbutyl radicals.

* * * * *